(12) United States Patent
Lee

(10) Patent No.: US 10,729,879 B2
(45) Date of Patent: Aug. 4, 2020

(54) SELF-CLEARING CATHETERS AND METHODS OF USE THEREOF

(71) Applicant: Hyowon Lee, West Lafayette, IN (US)

(72) Inventor: Hyowon Lee, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/054,398

(22) Filed: Feb. 26, 2016

(65) Prior Publication Data

US 2016/0250446 A1    Sep. 1, 2016

Related U.S. Application Data

(60) Provisional application No. 62/121,920, filed on Feb. 27, 2015.

(51) Int. Cl.
*A61M 25/00* (2006.01)

(52) U.S. Cl.
CPC ..... *A61M 25/0017* (2013.01); *A61M 25/0045* (2013.01); *A61M 2025/0019* (2013.01); *A61M 2025/0056* (2013.01); *A61M 2205/36* (2013.01); *Y10S 977/931* (2013.01)

(58) Field of Classification Search
CPC ...... A61M 25/0017; A61M 2025/0019; A61M 2205/368; A61M 2205/36
See application file for complete search history.

(56) References Cited

U.S. PATENT DOCUMENTS

| | | | | |
|---|---|---|---|---|
| 5,817,017 | A * | 10/1998 | Young | A61M 25/0108 600/433 |
| 6,560,477 | B1 * | 5/2003 | Filler | A61B 5/055 324/309 |
| 2004/0265233 | A1 * | 12/2004 | Holzer | B03C 1/01 424/9.32 |
| 2009/0022785 | A1 * | 1/2009 | Czerny | A61K 9/0009 424/451 |
| 2009/0081122 | A1 * | 3/2009 | Rufenacht | A61K 41/0052 424/1.29 |
| 2009/0179171 | A1 * | 7/2009 | Sailor | B82Y 25/00 252/62.51 R |
| 2012/0323318 | A1 * | 12/2012 | Yusuf | A61M 1/1053 623/3.11 |
| 2014/0093572 | A1 * | 4/2014 | Doktycz | B82Y 30/00 424/489 |
| 2015/0336096 | A1 * | 11/2015 | Smith | B03C 1/288 435/309.1 |

* cited by examiner

*Primary Examiner* — Rebecca E Eisenberg
*Assistant Examiner* — Tasnim Mehjabin Ahmed
(74) *Attorney, Agent, or Firm* — C. John Brannon; Brannon Sowers & Cracraft PC

(57) ABSTRACT

Methods and catheters suitable for removing or reducing the formation of cellular occlusion associated the catheters. The catheters include a surface coated or infused with magnetic nanoparticles. Once the catheter is implanted in a subject, the nanoparticles induce localized hyperthermia around the catheter in response to a magnetic field.

8 Claims, 5 Drawing Sheets

SELF-CLEARING CATHETERS AND METHODS OF USE THEREOF

CROSS-REFERENCE TO RELATED APPLICATIONS

This patent application claims priority to U.S. provisional patent application Ser. No. 62/121,920, filed on Feb. 27, 2015.

TECHNICAL FIELD

The present novel technology generally relates to medical devices, and, more particularly, to a catheter for reducing the likelihood of the formation of cellular occlusion at the site of central venous access.

BACKGROUND

Central venous catheters, also known as central venous access devices, have become a mainstay for patients requiring intravenous administration of medications and other therapies. Unlike peripheral intravenous catheters typically inserted into the veins of the hand or forearm, central access devices are inserted into large veins in the central venous circulatory system, for example into a large vein in the neck, chest, or groin. At present, central venous access devices have a relatively high failure rate, due in part to cellular obstructions or thrombus formation that can be lethal for patients.

For conditions such as hydrocephalus, one method to resolve these issues is in situ recanalization after revision surgery and in-patient neurosurgery. Alternately, for central venous access, full replacement of these implanted devices is often required. Often, patients need to be concomitantly treated with blood thinners, antibiotics and/or additional medications that may not otherwise be necessary and may likewise present other unwelcome side effects. Therefore, both of these processes come with additional cost, risk, and pain.

Accordingly, there is an ongoing need for improved catheters and like implantable devices that reduce the likelihood of formation of cellular occlusion at the site of central venous access devices in patients. The present novel technology addresses this need.

DETAILED DESCRIPTION

Figure 1:
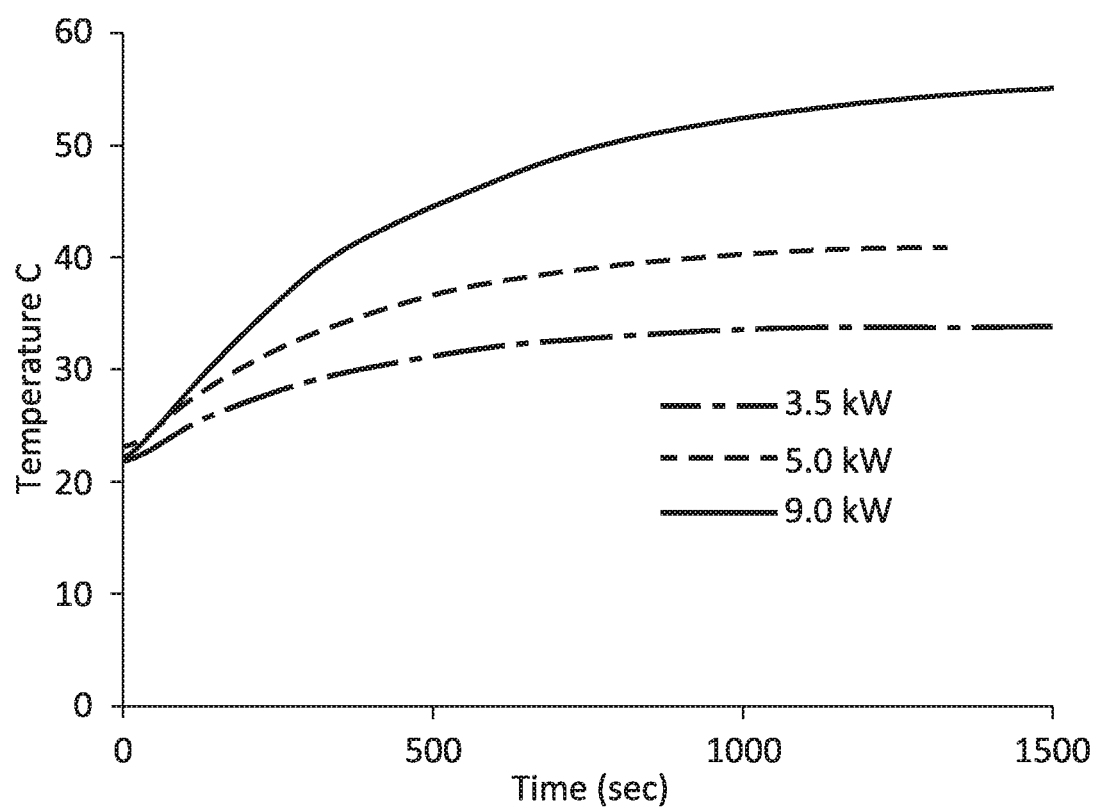
FIG. 1 graphically illustrates the relationship between heating time and temperature of a magnetically infused cannula according to a first embodiment the present novel technology for various power input levels.

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

The present novel technology relates to methods and devices by which the likelihood of formation of cellular occlusion at the site of central venous access devices in patients may be reduced.

Magnetic nanoparticle induced hyperthermia has been utilized in the treatment of cancer cells. Chronically implantable devices, such as ventricular catheters and central venous access devices, tend to have high failure rates due to mechanical cellular occlusion of the lumen and/or inlet pores. According to aspects of the present novel technology, chronically implantable catheters and like devices are coated or surface-infused with superparamagnetic nanoparticles. Once implanted in a subject, the nanoparticles may be energized to induce localized hyperthermia in and around the implanted devices to reduce and/or remove cellular obstructions, and thus prolong device lifetime. The superparamagnetic nanoparticles are typically magnetite ($Fe_3O_4$), maghemite ($\gamma$-$Fe_2O_3$), or the like and are typically provided from 10 to 100 nanometers in diameter, although the nanoparticles may be smaller than 10 nm or larger than 100 nm as desired.

The temperature of the superparamagnetic nanoparticles may be increased by applying an alternating magnetic field, typically characterized by a frequency between about 0.1 and about 2 MHz, more typically about 1.2 MHz. (See FIG. 1) The magnetic field strength is typically between about 3 and about 40 kA/m, although other weaker or stronger field strengths may be elected. The relationship between material property, frequency and amplitude of magnetic field is terms of power dissipation is described as follows: the volumetric power loss P, may be expressed as $P=\mu_o \pi \chi'' f H_o^2$, with the permeability of free space $\mu_o$, the second derivative of frequency and material dependent susceptibility $\chi''$, frequency f, and the applied magnetic field strength H.

Figure 2A:
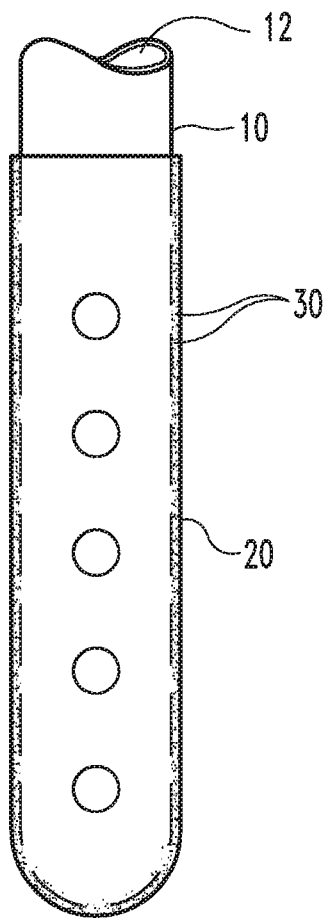
FIG. 2A is a schematic illustration of a cannula with a surface infusion of superparamagnetic nanoparticles according to the embodiment of FIG. 1.
Figure 2A:
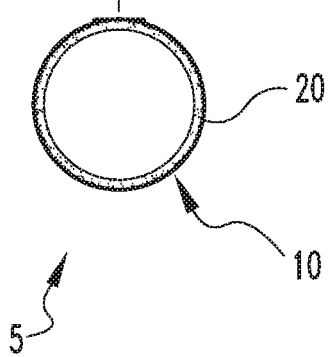
Figure 2B:
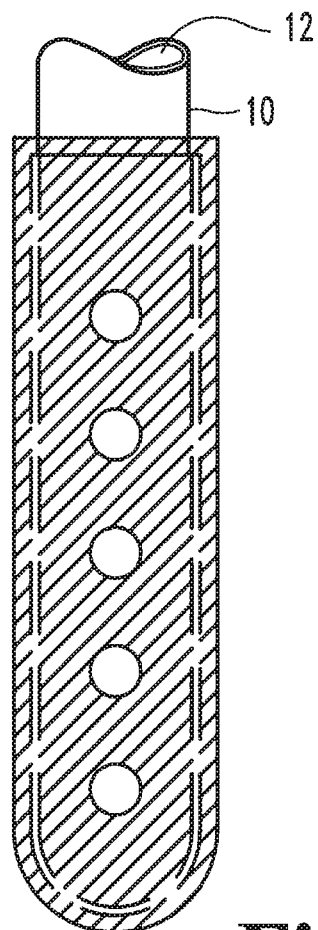
FIG. 2B is a schematic illustration of a cannula with a surface coating containing a dispersion of superparamagnetic nanoparticles according to the embodiment of FIG. 1.
Figure 2B:
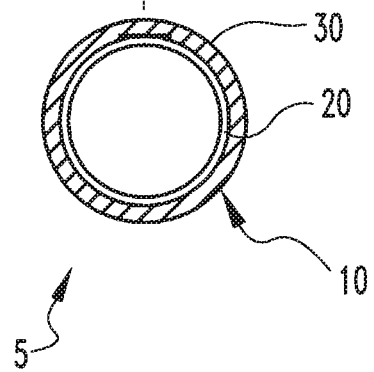
Figure 3A:
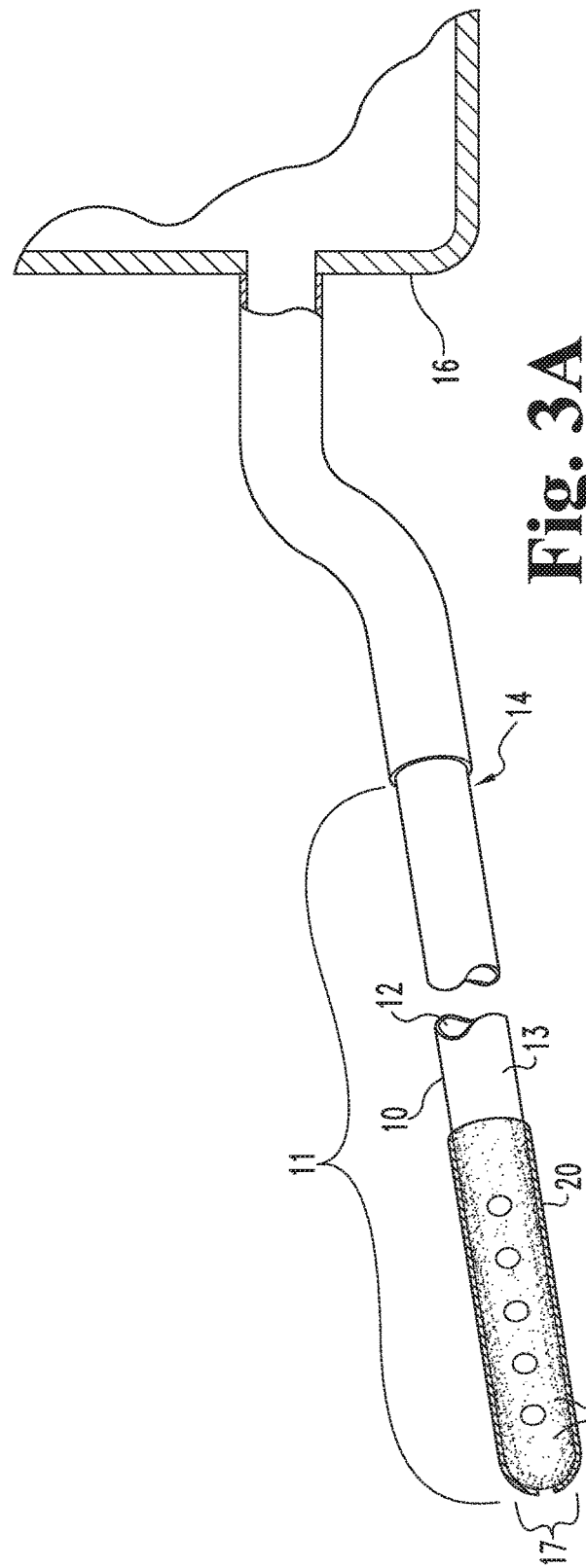
FIG. 3A is a schematic drawing of a cannula of FIG. 2 as connected to a fluid source.
Figure 3C:
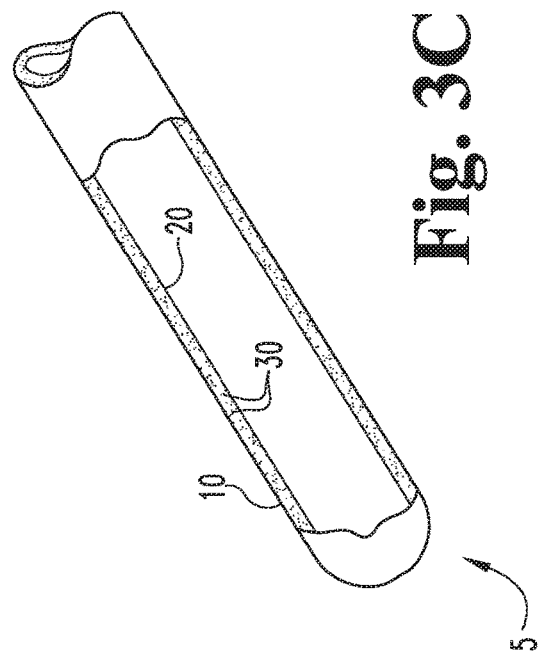
FIG. 3C is a schematic drawing of a cannula of FIG. 2 having an internal coating.
Figure 3B:
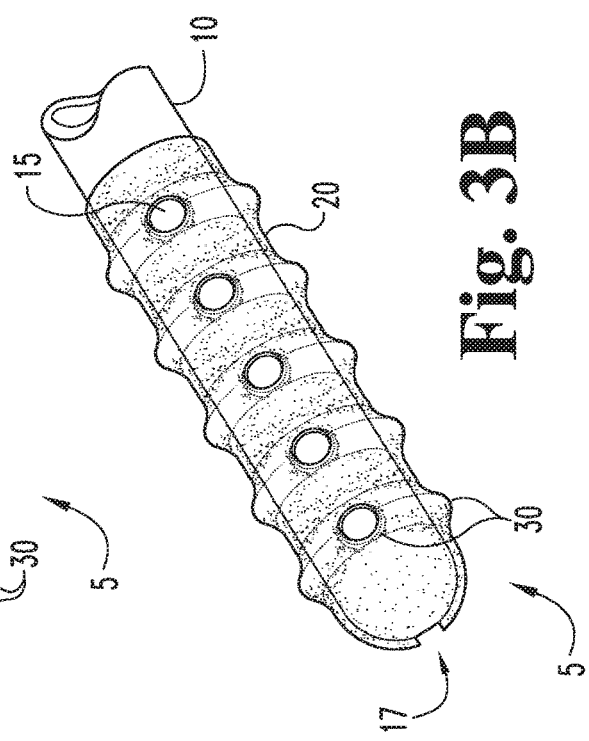
FIG. 3B is a schematic drawing of a cannula of FIG. 2 having a coating of uneven thickness and particulate concentration.
Figure 4:
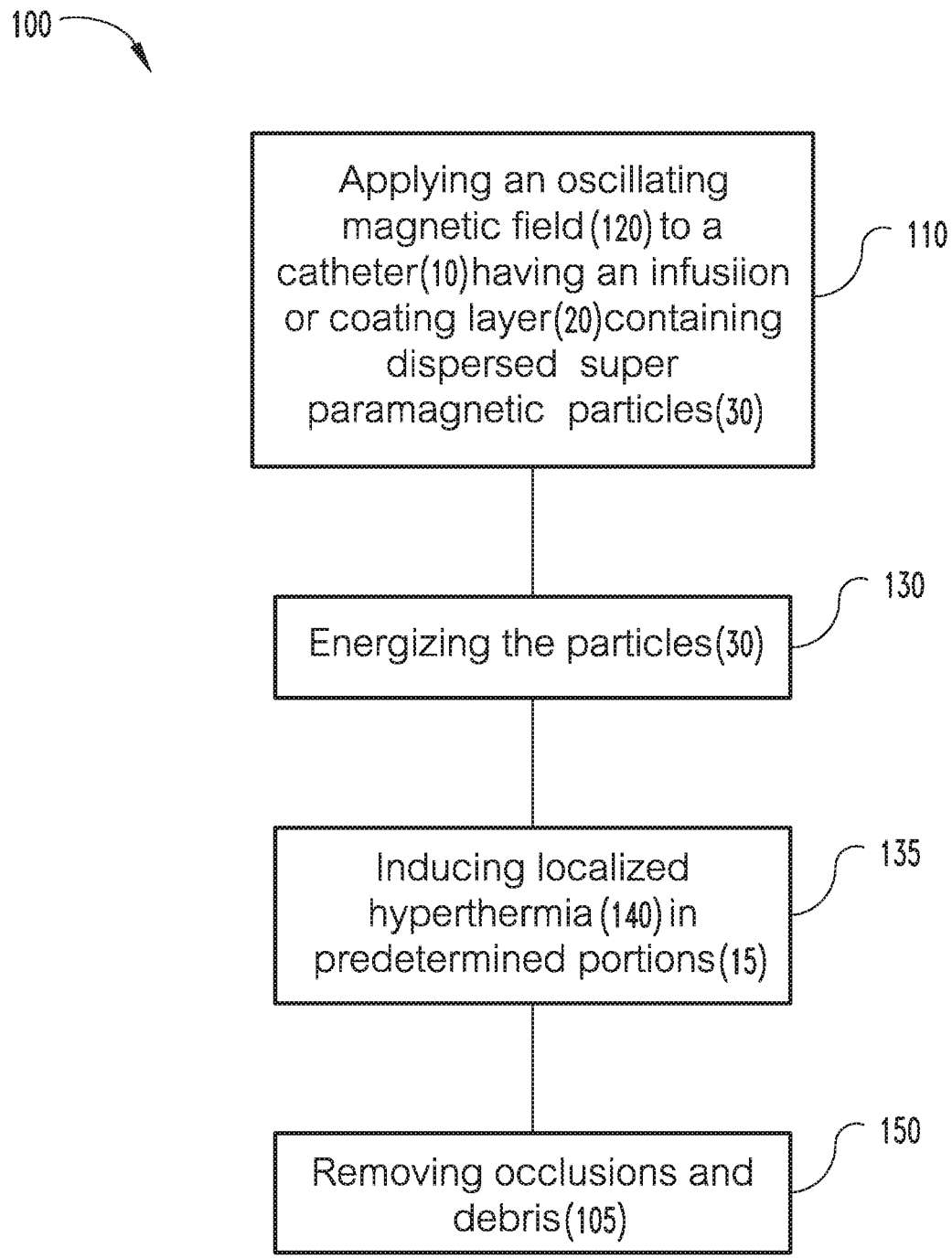
FIG. 4 is a process flow diagram of a method for clearing occlusions from an implantable device.
Figure 5:
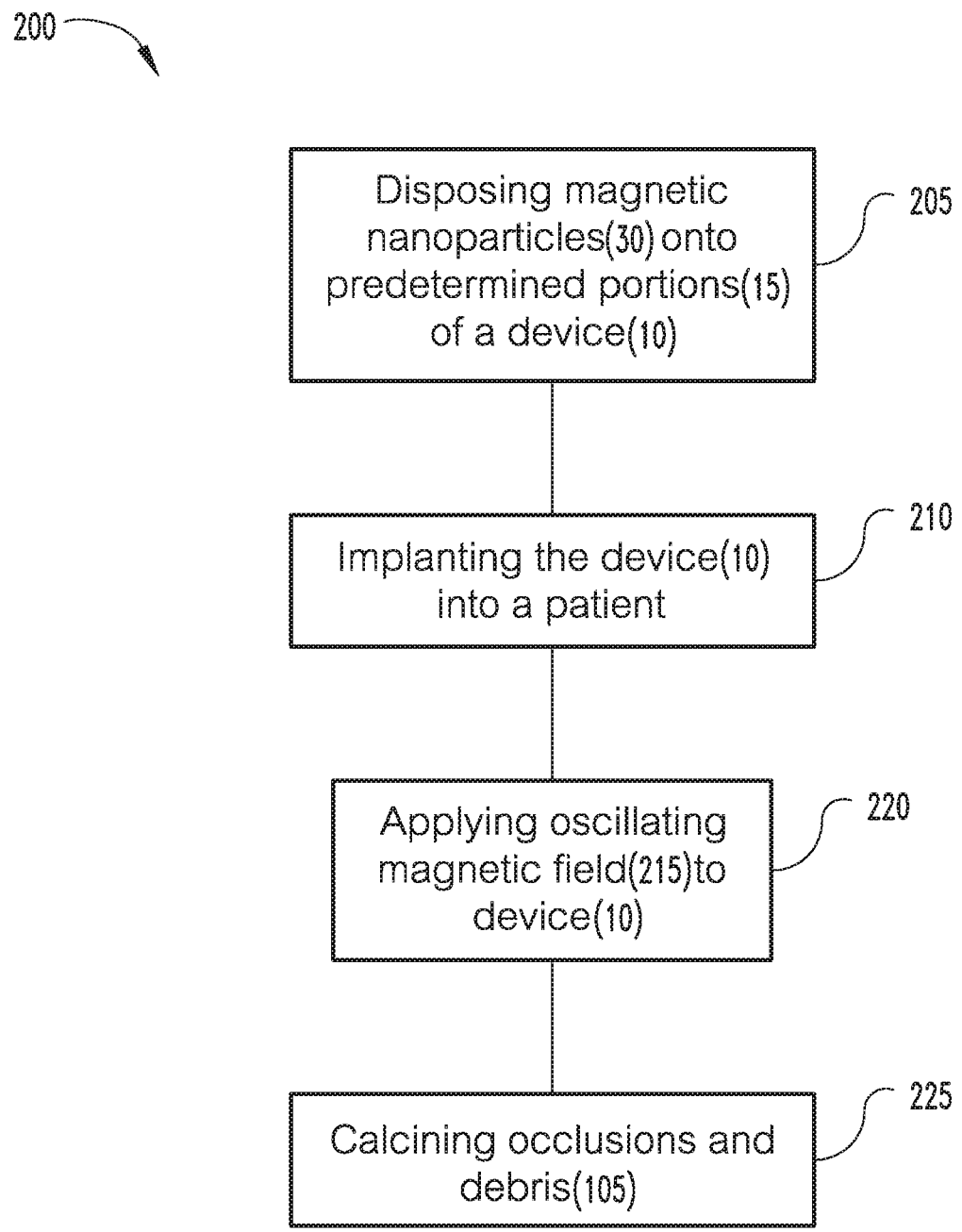
FIG. 5 is a process flow diagram of a method of preparing, inserting and in-situ cleaning an implantable device.

As shown in FIGS. 2A and 2B, chronically implantable catheters, such as ones used for hydrocephalous and central venous access, typically experience high failure rate due to cellular and thrombotic occlusions. Often, the failed devices need to be replaced to prevent the more serious side effects of hydrocephalus and catheter related thrombosis. The present novel technology relates to a system 5 for reducing clogging of catheters and like implantable devices 10. The system 5 operates by coating or infusing catheters, cannulas and like implantable devices 10 to define a layer or coating 20 containing magnetic nanoparticles 30, typically homogeneously distributed throughout, the implantable devices 10 may be locally superheated through interaction of an applied oscillating magnetic field with the magnetic nanoparticles 30 sufficiently to energize and heat the device 10 to remove or reduce the formation of cellular occlusions that interfere with the proper operation of these devices 10. A cannula 10 is typically defined by an elongated tube portion 11 having an inner surface 12 and an oppositely disposed outer surface 13. The device 10 typically has a first end 14 fluidically connectable to a fluid source 16 outside the patient and a second, oppositely disposed end 17 for fluidically communicating with the patient.

According to one aspect of the novel technology, a self-clearing catheter 10 includes at least one surface portion 15 coated or infused 20 with magnetic nanoparticles 30. The coated or infused surface portions 15 are typically positioned at or near the parts of the device 10 prone to occlusion by a build-up of cellular debris, such as openings, pores, ports, bends, junctions, or the like. Once the catheter 10 is implanted in a patient, the nanoparticles 30 may be energized by application of an oscillating magnetic field to induce localized hyperthermia at the site of the occlusion.

According to another aspect of the novel technology, a method 100 of removing or reducing the formation of cellular occlusion 105 associated with a catheter 10 implanted in a patient includes applying no a magnetic field 120 to the catheter 10 such that magnetic nanoparticles 30 on a surface 15 of the catheter 10 may be energized 130 to induce 135 localized hyperthermia 140 in and/or around predetermined portions 15 of the catheter 10. Such localized hyperthermia 140 reduces or removes 150 occlusions and/or built-up masses of cellular and like debris 105.

In view of the above, it can be seen that a significant advantage of this system 10 is that the nanoparticles 30 may be energized 130 to induce localized heat (hyperthermia) 140 and thereby remove an organic occlusion 105 and/or reduce or retard the formation of the same 105, resulting in the reduction of the need for revisional surgery or replacement of chronically implanted devices 10. The magnetic nanoparticles 30 may be energized in situ and are thus activated non-invasively.

In operation, one method 200 of removing, or reducing the formation of cellular occlusions 105 associated with a catheter 10 implanted in a patient includes disposing 205 a plurality of magnetic nanoparticles 30 on those portions or locations 15 of a catheter 10 predetermined to be at risk of clogging from accretions of cellular material 105. After the catheter 10 is implanted 210, and it is suspected that the catheter 10 has been or may be impaired by the formation or accretion of one or more cellular or organic masses 105 therein, an oscillating magnetic field 215 of predetermined strength and frequency is applied 220 to the catheter 10. The applied magnetic field 215 energizes 130 the magnetic nanoparticles 30 such that they generate heat 140, and the catheter 10 is heated to a high enough temperature to calcine 225 the cellular material 105 sufficiently to reduce or eliminate the clogging mass 105.

The magnetic nanoparticles 30 may be infused into the catheter body 10 so as to be unitary with the surface of the catheter 10 to define an infusion layer 20, thus yielding a composite material, may be applied to an already formed catheter 10 as a coating 20, or a combination of both. The coating 20 may be mixed in any biocompatible silicone dispersions, polyurethane, polyethylene, polyimide solution or the like which is applied, such as by dip coating, spray coating, or the like, and is typically then cured following coating. The concentration of the nanoparticles 30 typically ranges from 0.5-200 mg/ml, although lower or higher concentrations may be chosen as desired. The coating thickness typically ranges from 0.1-20 microns, but may be thinner or thicker.

The magnetic nanoparticles 30 are typically disposed likely to clog portions 15 of the catheter or cannula 10, such as around an opening in the catheter defining, when placed, a patient interface.

In some embodiments, for a catheter or cannula of a given size and composition, and thus with known and/or predetermined thermal properties, the magnetic nanoparticles 30 may be distributed in or on the cannula in a distribution pattern and/or concentration sufficient to define a maximum temperature to which an implanted cannula 30 may be heated by an oscillating magnetic field of a given strength and frequency, typically sufficient enough to calcine away clogs or obstructing masses, but insufficient to severely or permanently damage surrounding tissue.

Chronically implantable devices 10 include central venous access devices, hydrocephalus shunt system, implantable glucose sensors, biosensors, and like devices that may suffer from functional degradation due to biofouling be coated 20 according to the present novel technology to yield systems 10 that can be energized to combat biofouling. The coating matrix is typically applied via spray or dip coating techniques to yield a thin external membrane or layer 20 with the nanoparticles 30 suspended therein. In the case of dip coating, the inner lumen of the catheters may also be coated using low viscosity dip solution. The nanoparticles 30 are typically mixed homogeneously to provide uniform distribution of specific nanoparticle concentration to achieve predetermined temperature for biofouling removal, although nonhomogeneous distributions are contemplated to yield predetermined temperature gradients when energized.

It is possible to have nanoparticles or microparticles 30 infused into the implant body (typically mad of a polymer composition), which eliminates the need for coating process. In these variants, specific infusion depth may be better controlled and, typically, the superparamagnetic particles are positioned near the surface, more typically within 0.1 to 20 microns.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

I claim:

1. A self-clearing cannula for placement in a patient, comprising: an elongated tube portion having an inner surface and an oppositely disposed outer surface, a first end fluidically connectable to a fluid source outside the patient and a second, oppositely disposed end for fluidically communicating with the patient; plurality of magnetic nanoparticles operationally connected to at least a portion of the cannula; wherein the plurality of magnetic particles are positioned 20 microns from the outer surface; wherein the magnetic particles are present in a concentration 200 mg/ml; wherein the respective magnetic nanoparticles may be energized by an applied oscillating magnetic field with a field strength of 40 kA/m and with a frequency of 2 MHz to heat the cannula; wherein the respective magnetic nanoparticles are superparamagnetic particles larger than 100 nm in diameter.

2. The self-clearing cannula of claim 1 wherein the plurality of magnetic nanoparticles are infused into the cannula to define a composite material.

3. The self-clearing cannula of claim 1 and further comprising a coating matrix bonded to the cannula and defining the outer surface, wherein the respective magnetic nanoparticles are suspended in the coating matrix.

4. The self-clearing cannula of claim 3 wherein the coating matrix is between 0.1 micron and 20 microns in thickness.

5. The self-clearing cannula of claim 1 wherein the plurality of magnetic nanoparticles are disposed at the second end.

6. A self-cleaning cannula device comprising:
   an elongated tube portion defining an inner surface and an oppositely disposed outer surface and a first end fluidically connectable to a fluid source and a second, oppositely disposed end for fluidically communicating with a patient; and
   a plurality of superparamagnetic nanoparticles operationally connected to at least a portion of the cannula;
   wherein the plurality of superparamagnetic particles are positioned 20 microns from the inner surface;
   wherein each superparamagnetic particle is greater than 100 nm in diameter;
   wherein the superparamagnetic particles are present in a concentration of 200 mg/ml;
   wherein the respective superparamagnetic nanoparticles may be energized by an applied oscillating magnetic field with a frequency of about 2 MHz to heat the cannula.

7. The self-cleaning cannula device of claim 6 wherein the superparamagnetic nanoparticles are maghemite particles and wherein the magnetic field has a frequency of 2 MHz.

8. A self-cleaning cannula apparatus comprising:
   an elongated tube portion defining an inner surface and an oppositely disposed outer surface and a first end fluidically connectable to a fluid source and a second, oppositely disposed end for fluidically communicating with a patient; and
   a plurality of superparamagnetic nanoparticles operationally connected to at least a portion of the cannula;
   wherein the plurality of superparamagnetic particles are positioned and 20 microns from a respective surface;
   wherein each superparamagnetic particle is greater than 100 nm in diameter;
   wherein the superparamagnetic particles are present in a concentration of 200 mg/ml;
   wherein the respective superparamagnetic nanoparticles may be energized by an applied oscillating magnetic field with a field strength of 40 kA/m.

* * * * *